United States Patent
Nishimoto et al.

(10) Patent No.: US 10,687,754 B2
(45) Date of Patent: Jun. 23, 2020

(54) BRAIN ACTIVITY MEASURING APPARATUS AND BRAIN ACTIVITY MEASURING METHOD

(71) Applicant: Advanced Telecommunications Research Institute International, Soraku-gun, Kyoto (JP)

(72) Inventors: Hironori Nishimoto, Soraku-gun (JP); Takanori Kochiyama, Soraku-gun (JP); Yasuhiro Shimada, Soraku-gun (JP); Ichirou Fujimoto, Soraku-gun (JP)

(73) Assignee: ADVANCED TELECOMMUNICATIONS RESEARCH INSTITUTE INTERNATIONAL, Soraku-Gun, Kyoto (JP)

(*) Notice: Subject to any disclaimer, the term of this patent is extended or adjusted under 35 U.S.C. 154(b) by 833 days.

(21) Appl. No.: 14/778,945

(22) PCT Filed: Mar. 18, 2014

(86) PCT No.: PCT/JP2014/057353
§ 371 (c)(1),
(2) Date: Sep. 21, 2015

(87) PCT Pub. No.: WO2014/148495
PCT Pub. Date: Sep. 25, 2014

(65) Prior Publication Data
US 2016/0045149 A1    Feb. 18, 2016

(30) Foreign Application Priority Data
Mar. 22, 2013   (JP) .................................. 2013-059990

(51) Int. Cl.
*A61B 5/00*    (2006.01)
*A61B 5/055*   (2006.01)
(Continued)

(52) U.S. Cl.
CPC ............ *A61B 5/4064* (2013.01); *A61B 5/055* (2013.01); *A61B 5/486* (2013.01); *A61B 5/7257* (2013.01);
(Continued)

(58) Field of Classification Search
CPC . A61B 2576/026; A61B 5/055; A61B 5/4064; A61B 5/486; A61B 5/7257;
(Continued)

(56) References Cited

U.S. PATENT DOCUMENTS 5,514,957 A     5/1996 Tatebayashi
9,928,379 B1 *  3/2018 Hoffer ................. G06F 21/6245
(Continued)

FOREIGN PATENT DOCUMENTS

JP   2004-024918 A    1/2004
JP   2004-294593 A   10/2004
(Continued)

OTHER PUBLICATIONS

Thesen et al., "Prospective Acquisition Correction for Head Motion With Image-Based Tracking for Real-Time fMRI," Magnetic Resonance in Medicine, vol. 44, No. 3, Sep. 1, 2000, XP000951988, pp. 457-465.
(Continued)

*Primary Examiner* — Michael T Rozanski
(74) *Attorney, Agent, or Firm* — Birch, Stewart, Kolasch & Birch, LLP

(57) ABSTRACT

[Object] An object is to provide a brain activity measuring apparatus and a brain activity measuring method that can precisely ensure reproducibility of measurements for a plurality of measurements made separately for a number of times using functional magnetic resonance imaging.
[Solution] In an MRI apparatus 10, a data processing unit 32 determines rigid transformation between an original tomo-
(Continued)

graphic image obtained in a past measurement and stored in a storage unit 36 and a pilot tomographic image obtained in a present imaging session such that mutual information between the original and pilot tomographic images is locally maximized; and based on a parameter of the determined rigid transformation, position and direction of a slice image of the tomographic image in the present imaging session are corrected.

6 Claims, 11 Drawing Sheets

(51) Int. Cl.
*G01R 33/56* (2006.01)
*G01R 33/54* (2006.01)
G01R 33/483 (2006.01)
G01R 33/48 (2006.01)

(52) U.S. Cl.
CPC ....... *G01R 33/543* (2013.01); *G01R 33/5608* (2013.01); *A61B 2576/026* (2013.01); *G01R 33/4806* (2013.01); *G01R 33/4835* (2013.01)

(58) Field of Classification Search
CPC ............ G01R 33/4806; G01R 33/4835; G01R 33/543; G01R 33/5608
See application file for complete search history.

(56) References Cited

U.S. PATENT DOCUMENTS

| | | |
|---|---|---|
| 2002/0032377 A1 | 3/2002 | Thesen |
| 2004/0191747 A1 | 9/2004 | Atsumori et al. |
| 2005/0206379 A1 | 9/2005 | Kojima |
| 2009/0116761 A1 | 5/2009 | Wheaton et al. |
| 2010/0129005 A1 | 5/2010 | Tao et al. |
| 2011/0028827 A1 | 2/2011 | Sitaram et al. |
| 2011/0258313 A1* | 10/2011 | Mallik ................. H04W 8/005 709/224 |

FOREIGN PATENT DOCUMENTS

| | | |
|---|---|---|
| JP | 2004-321211 A | 11/2004 |
| JP | 2005-296627 A | 10/2005 |
| JP | 2007-264055 A | 10/2007 |
| JP | 2009-28147 A | 2/2009 |
| JP | 2010-125329 A | 6/2010 |
| JP | 2011-000184 A | 1/2011 |

OTHER PUBLICATIONS

Laconte, "Decoding fMRI brain states in real-time," NeuroImage, vol. 56, 2011 (available online Jun. 30, 2010), pp. 440-454.

Collignon et al., "Automated Multi-Modality Image Registration Based on Information Theory", Information processing in medical imaging, vol. 3, Issue 6, pp. 263-274, 1995.

Kamitani et al., "Decoding the visual and subjective contents of the human brain", Neuroscience, 8, pp. 679-685, 2005.

Maes et al., "Multimodality Image Registration by Maximization of Mutual Information", IEEE Transactions on Medical Imaging, vol. 16, No. 2, pp. 187-198, Apr. 1997.

Shibata et al., "Perceptual Learning Incepted by Decoded fMRI Neurofeedback Without Stimulus Presentation", Science vol. 334, Dec. 9, 2011.

Shinohara et al., (Basics of Tomographic Imaging, 20th Lecture, Mutual Information of Images), Journal of Japanese Association of Tomography, vol. 33, No. 3, pp. 154-160.

Watanabe et al., "Greater plasticity in lower-level than higher-level visual motion processing in a passive perceptual learning task", Nature Neuroscience, 5, pp. 1003-1009, 2002.

Weiskopf, "Real-time fMRI and its application to neurofeedback", NeuroImage 62, pp. 682-692, 2012.

Shibata et al., "Perceptual Learning Incepted by Decoded fMRI Neurofeedback Without Stimulus Presentation," Science, vol. 334, Dec. 9, 2011, pp. 1413-1415.

* cited by examiner

BRAIN ACTIVITY MEASURING APPARATUS AND BRAIN ACTIVITY MEASURING METHOD

TECHNICAL FIELD

The present invention relates to a brain activity measuring apparatus and a brain activity measuring method.

BACKGROUND ART

Recently, training systems for training a subject utilizing the technology of computer graphics (CG) such as virtual reality (VR) are available (for example, see Japanese Patent Laying-Open No. 2004-294593 (hereinafter referred to as '593 Reference) and Japanese Patent Laying-Open No. 2007-264055 (hereinafter referred to as '055 Reference)). A training supporting apparatus disclosed in '593 Reference detects, as the biological reaction of the subject, an active region of his/her brain using near infrared light, to assist rehabilitation and image training of a subject with disabilities. The training supporting apparatus measures an active region or regions of the subject's brain while the subject is working on a calculation problem or a memory task imposed as a training material, and after the training, the effectiveness of the training is confirmed. '055 Reference discloses a training system that always keeps an optimal training scenario in accordance with the biological reaction of a subject during training.

Such a technique of scientifically grasping physiological indexes that would not otherwise be sensed and feeding these back to enable perception by the subject is referred to as "bio-feedback." Though conventional bio-feedback sometimes utilizes biological information such as pulse and breath, it mainly involves converting human brain wave outputs into visible images or audible sounds and feeding them back to humans. A subject can grasp the state of his/her brain waves on real-time basis. Therefore, bio-feedback is helpful for the subject to control the state of his/her own brain waves.

Human sensory and esthesic systems are ever-changing in accordance with the surrounding environment. Most of the changes occur in a certain early period of human developmental stage, or the period referred to as a "critical period." Adults, however, still keep sufficient degree of plasticity of sensory and esthesic systems to adapt to significant changes in surrounding environment. By way of example, it is reported, by Watanabe et al., that adults subjected to a training using specific esthesic stimulus or exposed to specific esthesic stimulus have improved performance for the training task or improved sensitivity to the esthesic stimulus, and that such results of training were maintained for a few months to a few years (T. Watanabe, J. E. Nanez Sr., S. Koyama, I. Mukai, J. Liederman and Y. Sasaki: Greater plasticity in Lower-level than higher-level visual motion processing in a passive perceptual learning task. Nature Neuroscience, 5, 1003-1009, 2002). Such a change is referred to as sensory learning, and it has been confirmed that such a change occurs in every sensory organ, that is, vision, audition, olfaction, gustation, and taction.

Nikolaus Weiskopf reports an example of bio-feedback applying fMRI (functional Magnetic Resonance Imaging), which is a method of visualizing hemodynamic reactions related to human brain activities utilizing MRI (Magnetic Resonance Imaging), rather than the brain waves (Nikolaus Weiskopf, "Real-time fMRI and its application to neurofeedback", NeuroImage 62 (2012) 682-692). Further, Shibata et al. report one such type of feedback method, in which a stimulus as an object of learning is not directly applied to a subject while brain activities are detected and decoded and only the degree of approximation to a desired brain activity is fed back to the subject to enable "sensory learning." (Kazuhisa Shibata, Takeo Watanabe, Yuka Sasaki, Mitsuo Kawato, "Perceptual Learning Incepted by Decoded fMRI Neurofeedback Without Stimulus Presentation", SCIENCE VOL 334 9 Dec. 2011). Such a method of bio-feedback is referred to as DecNef method (Decoded NeuroFeedback method).

Nuclear Magnetic Resonance Imaging as such will be briefly described in the following.

Conventionally, as a method of imaging cross-sections of the brain or the whole body of a living body, nuclear magnetic resonance imaging has been used, for example, for human clinical diagnostic imaging, which method utilizes nuclear magnetic resonance with atoms in the living body, particularly with atomic nuclei of hydrogen atoms.

As compared with "X-ray CT," which is a similar method of human tomographic imaging, characteristics of nuclear magnetic resonance imaging when applied to a human body, for example, are as follows:

(1) An image density distribution reflecting distribution of hydrogen atoms and their signal relaxation time (reflecting strength of atomic bonding) are obtained. Therefore, the shadings present different nature of tissues, making it easier to observe difference in tissues;

(2) The magnetic field is not absorbed by bones. Therefore, a portion surrounded by a bone or bones (for example, inside one's skull, or spinal cord) can easily be observed; and (3) Unlike X-ray, it is not harmful to human body and, hence, it has a wide range of possible applications.

Nuclear magnetic resonance imaging described above uses magnetic property of hydrogen atomic nuclei (protons), which are most abundant in human cells and have highest magnetism. Motion in a magnetic field of spin angular momentum associated with the magnetism of hydrogen atomic nucleus is, classically, compared to precession of spin of a spinning top.

In the following, as a description of background of the present invention, the principle of magnetic resonance will be summarized using the intuitive classical model.

The direction of spin angular momentum of hydrogen atomic nucleus (direction of axis of rotation of spinning top) is random in an environment free of magnetic field. When a static magnetic field is applied, however, the momentum is aligned with the line of magnetic force.

In this state, when an oscillating magnetic field is superposed and the frequency of oscillating magnetic field is resonance frequency $f0=\gamma B0/2\pi$ ($\gamma$: substance-specific coefficient) determined by the intensity of static magnetic field, energy moves to the side of atomic nuclei because of resonance, and the direction of magnetic vector changes (precession increases). When the oscillating magnetic field is turned off in this state, the precession gradually returns to the direction in the static magnetic field with the tilt angle returning to the previous angle. By externally detecting this process by an antenna coil, an NMR signal can be obtained.

The resonance frequency f0 mentioned above of hydrogen atom is $42.6 \times B0$ (MHz) where B0 (T) represents the intensity of the static magnetic field.

Further, in nuclear magnetic resonance imaging, using changes appearing in detected signals in accordance with changes in the blood flow, it is possible to visualize an active portion of a brain activated in response to an external stimulus. Such a nuclear magnetic resonance imaging is specifically referred to as fMRI (functional MRI).

An fMRI uses a common MRI apparatus with additional hardware and software necessary for fMRI measurement.

The change in blood flow causes change in NMR signal intensity, since oxygenated hemoglobin has magnetic property different from that of deoxygenated hemoglobin. Hemoglobin is diamagnetic when oxygenated, and it does not have any influence on relaxation time of hydrogen atoms in the surrounding water. In contrast, hemoglobin is paramagnetic when deoxygenated, and it changes surrounding magnetic field. Therefore, when the brain receives any stimulus and local blood flow increases and oxygenated hemoglobin increases, the change can be detected by the MRI signals. The stimulus to a subject may include visual stimulus, audio stimulus, or performance of a prescribed task, as disclosed, for example, in Japanese Patent Laying-Open No. 2011-000184.

In the studies of brain functions, brain activities are measured by measuring increase in nuclear magnetic resonance signal (MRI signal) of hydrogen atoms corresponding to a phenomenon that density of deoxygenated hemoglobin in red blood cells decrease in minute vein or capillary vessel (BOLD effect).

Particularly, in studies related to human motor function, brain activities are measured by the MRI apparatus as described above while a subject or subjects are performing some physical activity. The operation (task) to be done by the subject may include, for example, an operation of gripping some object. While the subject grips a detecting portion of a grip force detecting device, the force exerted on the grip force detecting device is detected and brain activities of the subject during the gripping operation are measured by the above-mentioned MRI apparatus.

For human subjects, non-invasive measurement of brain functions is essential. In this aspect, decoding technique enabling extraction of more detailed information from fMRI data has been developed (Kamitani Y, Tong F. Decoding the visual and subjective contents of the human brain, Nat Neurosci, 2005; 8: 679-85). The above-described DecNef is an application of such a decoding technique to a task related to sensory learning.

SUMMARY OF INVENTION

Technical Problem

The above-described DecNef method, however, requires decoding of changes in brain activities measured by the functional Magnetic Resonance Imaging on real-time or near-real-time basis. In addition, the subject must go through the task a number of times separately for a number of days while receiving the feedback of decoded results. Here, it is not necessarily the case that the position and direction of the subject's head with respect to the apparatus are the same in every session. Further, to ensure precision of the plurality of tasks that take days, it is essential that the measurement signals from the MRI apparatus can be collected with high reproducibility at every session.

It is noted that the MRI apparatus is basically a medical instrument. Therefore, an MRI apparatus installed, for example, at an institution may be used by a clinical laboratory technician of the institution to do inspections of a patient, and such a use may involve privacy information of the patient. The MRI apparatus may also be used by a doctor or a researcher of a different institution for experimental, research or clinical study. Such a mixed manner of operation of the apparatus must adequately address patients' privacy concerns.

Further, assume that the MRI apparatus is used by a doctor or a researcher of a different institution. It may be the case that the intended study cannot be completed by a built-in computer or the like originally provided in the MRI apparatus and extra work on a computer or the like other than the built-in computer may be required. A system is necessary that ensures even in such a situation that the data obtained by the MRI apparatus are constantly available to other computer or the like and ensures that the built-in computer or the like originally provided in the apparatus is free from the influence of the other apparatuses.

The present invention was made to solve the above-described problems and its object is to provide a brain activity measuring apparatus and a brain activity measuring method that can precisely ensure reproducibility of measurements for a plurality of measurements made separately for a number of times using functional magnetic resonance imaging.

Another object of the present invention is to provide a brain activity measuring apparatus and a brain activity measuring method that can be stably operated and can protect privacy of patients even when operated by a plurality of operators.

Solution to Problem

According to an aspect, the present invention provides a brain activity measuring apparatus detecting a detection signal caused by nuclear magnetic resonance from a subject, for generating a tomographic image of a region to be measured. The brain activity measuring apparatus includes: a static magnetic field applying device for applying a static magnetic field to the region to be measured; a magnetic field gradient applying device for applying to the region to be measured a magnetic field modulated such that the detection signal comes to have positional information of an atomic nucleus emitting the detection signal in a selected cross-section of the region to be measured; an electro-magnetic wave transmitting/receiving device for applying an electromagnetic wave to the region to be measured and detecting the detection signal from the region to be measured; a tomography control device for applying the electro-magnetic wave to the electro-magnetic wave transmitting/receiving device and receiving the detection signal to generate the tomographic image of a slice; and a storage device for storing the obtained tomographic image. The tomography control device i) determines three-dimensional rigid transformation between a reference tomographic image of the subject obtained in a past measurement and stored in the storage device and a preliminary tomographic image of the subject obtained in a present imaging session such that mutual information between the reference tomographic image and the preliminary tomographic image is locally maximized, and ii) based on a parameter of the determined rigid transformation, controls the magnetic field gradient applying device in the present imaging session and thereby corrects position and direction of a slice of tomographic imaging.

Preferably, the tomography control device corrects a position of the slice in a coordinate system of the brain activity measuring apparatus, based on a parameter of the rigid transformation determined in a coordinate system of a tomographic image by the reference tomographic image and the preliminary tomographic image.

Preferably, the brain activity measuring apparatus further includes a presenting device for providing bio-feedback to the subject based on the obtained tomographic image.

Preferably, the bio-feedback is bio-feedback based on decoded neuro-feedback method.

Preferably, the brain activity measuring apparatus further includes a network interface for communicating with a relay server through a first network. The relay server transfers the tomographic image data transferred through the network interface to a terminal device through a second network independent from the first network.

According to another aspect, the present invention provides a brain activity measuring method, detecting a detection signal caused by nuclear magnetic resonance from a subject, for generating a tomographic image of a region to be measured. The brain activity measuring method includes the steps of: applying a static magnetic field to the region to be measured; applying to the region to be measured a magnetic field modulated such that the detection signal comes to have positional information of an atomic nucleus emitting the detection signal in a selected cross-section of the region to be measured; applying an electro-magnetic wave to the region to be measured and detecting the detection signal from the region to be measured; an operating device receiving the detection signal and generating the tomographic image of a slice; and storing the obtained tomographic image in a storage device. The step of the operating device generating the tomographic image includes the steps of determining three-dimensional rigid transformation between a reference tomographic image of the subject obtained in a past measurement and stored in the storage device and a preliminary tomographic image of the subject obtained in a present imaging session such that mutual information between the reference tomographic image and the preliminary tomographic image is locally maximized; and based on a parameter of the determined rigid transformation, controlling the magnetic field gradient applying device and thereby correcting position and direction of a slice of tomographic imaging.

Preferably, at the correcting step, the operating device corrects a position of the slice in a coordinate system of the brain activity measuring apparatus, based on a parameter of the rigid transformation determined in a coordinate system of a tomographic image by the reference tomographic image and the preliminary tomographic image.

More preferably, the brain activity measuring apparatus includes a network interface for communicating with a relay server through a first network. The brain activity measuring method further includes the step of the relay server transferring the tomographic image data transferred through the network interface to a terminal device through a second network independent from the first network.

Advantageous Effects of Invention

By the present invention, it becomes possible to exactly ensure the reproducibility of measurements performed a number of times separately by the functional magnetic resonance imaging.

Further, the present invention enables stable operation even when operated by a plurality of operators and thereby enables protection of patients' privacy.

DESCRIPTION OF EMBODIMENTS

Figure 1:
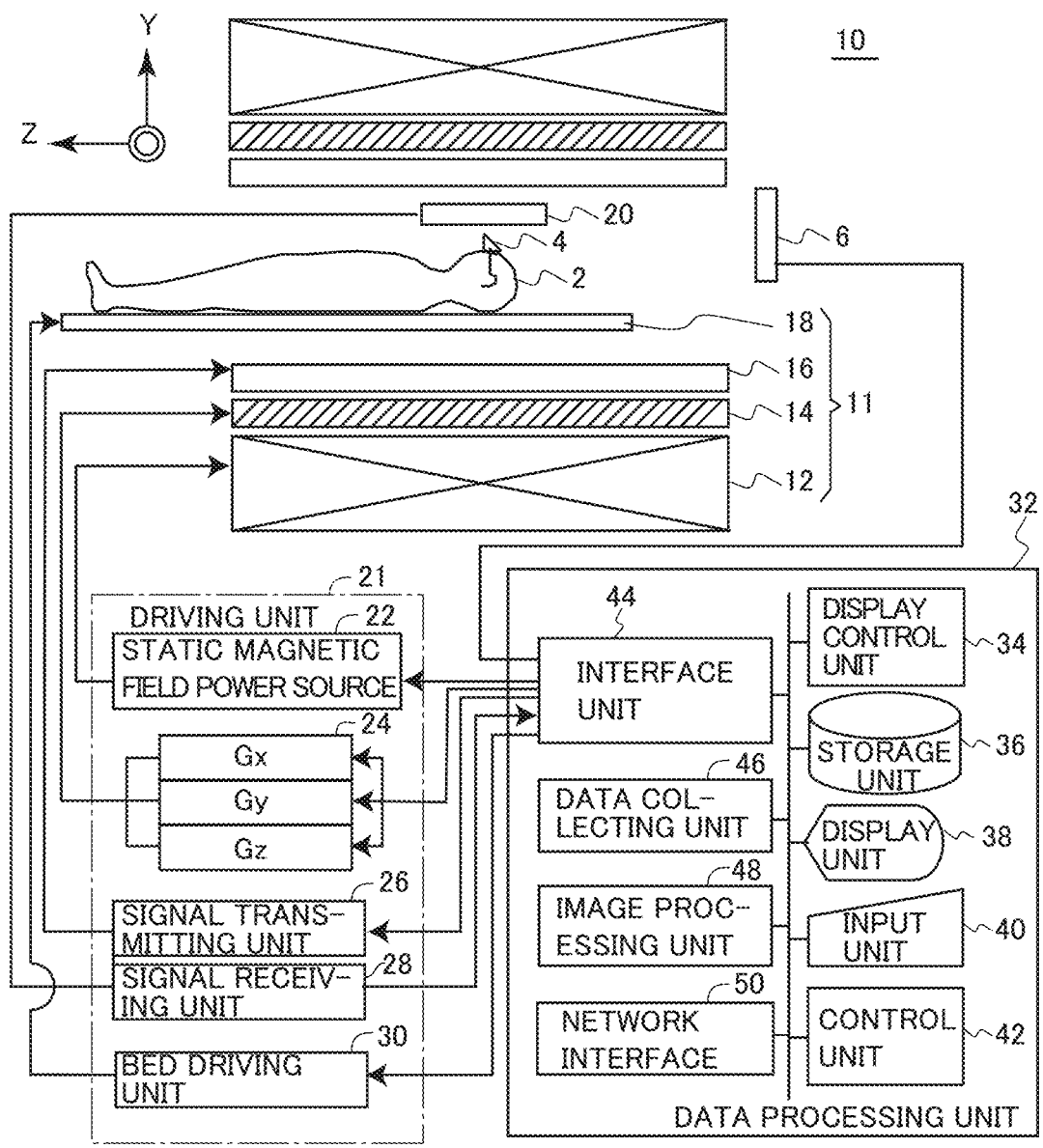
FIG. 1 is a schematic diagram showing an overall configuration of an MRI apparatus 10.

In the following, a configuration of an MRI system in accordance with embodiments of the present invention will be described with reference to the drawings. In the embodiments below, components or process steps denoted by the same reference characters are the same or corresponding components or steps and, therefore, description thereof will not be repeated unless necessary.

First Embodiment

FIG. 1 is a schematic diagram showing an overall configuration of an MRI apparatus 10.

Referring to FIG. 1, MRI apparatus 10 includes: a magnetic field applying mechanism 11 applying a controlled magnetic field to, and irradiating with RF wave, a region of interest of a subject 2; a receiving coil 20 receiving a response wave (NMR signal) from subject 2 and outputting an analog signal; a driving unit 21 controlling the magnetic field applied to subject 2 and controlling transmission/reception of RF wave; and a data processing unit 32 configuring a control sequence of driving unit 21 and processing various data signals to generate an image.

Here, a central axis of a cylindrical bore in which subject 2 is placed is regarded as a Z-axis, and a horizontal direction orthogonal to the Z-axis and the vertical direction orthogonal to the Z-axis are defined as X-axis and Y-axis, respectively.

In MRI apparatus 10 having such a configuration, because of the static magnetic field applied by magnetic field applying mechanism 11, nuclear spins of atomic nuclei forming subject 2 are oriented in the direction of magnetic field (Z-axis) and perform precession with the direction of magnetic field being an axis, with Larmor frequency unique to the atomic nuclei.

When irradiated with an RF pulse of the same Larmor frequency, the atoms resonate, absorb energy and are excited, resulting in nuclear magnetic resonance (NMR). When the irradiation with RF pulse is stopped after the resonance, the atoms discharge energy and return to the original, steady state. This process is referred to as a relaxation process. In the relaxation process, the atoms output electromagnetic wave (NMR signal) having the same frequency as the Larmor frequency.

The output NMR signal is received by receiving coil 20 as a response wave from subject 2, and the region of interest of subject 2 is imaged by data processing unit 32.

Magnetic field applying mechanism 11 includes a static magnetic field generating coil 12, a magnetic field gradient generating coil 14, an RF irradiating unit 16, and a bed 18 for placing subject 2 in the bore.

By way of example, subject 2 lies on his/her back on bed 18. Though not limited, subject 2 may view an image displayed on a display 6 mounted vertical to the Z-axis, using prism glasses 4. Visual stimulus is applied to subject 2 by an image on display 6. In another embodiment, visual stimulus to subject 2 may be applied by projecting an image in front of subject 2 using a projector.

Such a visual stimulus corresponds to presentation of feedback information in the above-described bio-feedback. Particularly, in DecNef method, based on the functional image from fMRI, brain activities are detected and decoded, and only the degree of similarity to a desired brain activity is fedback to the subject.

Driving unit 21 includes a static magnetic field power source 22, a magnetic field gradient power source 24, a signal transmitting unit 26, a signal receiving unit 28, and a bed driving unit 30 for moving bed 18 to any position along the Z-axis.

Data processing unit 32 includes: an input unit 40 for receiving various operations and information input from an operator (not shown); a display unit 38 for displaying various images and various pieces of information related to the region of interest of subject 2, on a screen; a display control unit 34 for controlling display of display unit 38; a storage unit 36 for storing programs to cause execution of various processes, control parameters, image data (structural images and the like as will be described later) and other electronic data; a control unit 42 controlling operations of various functional units, including generating a control sequence for driving the driving unit 21; an interface unit 44 for executing transmission/reception of various signals to/from driving unit 21; a data collecting unit 46 for collecting data consisting of a group of NMR signals derived from the regions of interest; an image processing unit 48 for forming an image based on the data of NMR signals; and a network interface 50 for executing communication with a network.

Data processing unit 32 may be a dedicated computer, or it may be a general purpose computer executing functions of causing operations of various functional units, in which designated operations, data processing and generation of control sequence are realized by a program or programs stored in storage unit 36. In the following, description will be given assuming that data processing unit 32 is implemented by a general purpose computer.

Static magnetic field generating coil 12 causes a current supplied from a static magnetic field power source 22 to flow through a helical coil wound around the Z-axis to generate an induction magnetic field, and thereby generates a static magnetic field in the Z-direction in the bore. The region of interest of subject 2 is placed in the region of highly uniform static magnetic field formed in the bore. More specifically, here, static magnetic field generating coil 12 is comprised of four air core coils, forms a uniform magnetic field inside by the combination of the coils, and attains orientation of the spins of prescribed atomic nuclei in the body of subject 2, or more specifically, the spins of hydrogen atomic nuclei.

Magnetic field gradient generating coil 14 is formed of X-, Y- and Z-coils (not shown), and provided on an inner peripheral surface of cylindrical static magnetic field generating coil 12.

These X-, Y- and Z-coils superpose magnetic field gradients on the uniform magnetic field in the bore with the X-axis, Y-axis and Z-axis directions switched in turn, whereby creating intensity gradient in the static magnetic field. When excited, the Z-coil tilts the magnetic field intensity to the Z-direction and thereby defines a resonance surface; the Y-coil applies a tilt for a short period of time immediately after application of the magnetic field in the Z-direction, and thereby adds phase modulation in proportion to the Y-coordinate, to the detected signal (phase encoding); and thereafter the X-coil applies a tilt when data is collected, and thereby adds frequency modulation in proportion to the X-coordinate, to the detected signal (frequency encoding).

The switching of superposed magnetic field gradients is realized as different pulse signals are output to the X-, Y- and Z-coils from the magnetic field gradient power source 24 in accordance with a control sequence. Thus, the position of subject 2 expressed by the NMR can be specified, and positional information in three-dimensional coordinates necessary for forming an image of subject 2 are provided.

Here, using the orthogonally crossing three sets of magnetic field gradients, allocating slice direction, phase encoding direction and frequency encoding direction to the magnetic fields respectively and by combining these, images can be taken from various angles. By way of example, in addition to transverse slice in the same direction as taken by an X-ray CT apparatus, sagittal and coronal slices orthogonal thereto, as well as an oblique slice, of which direction vertical to its plane is not parallel to any of the axes of three orthogonally crossing magnetic field gradients, can be imaged. Control for setting the positions and orientation (tilt) of these slice planes is disclosed in Japanese Patent Laying-Open No. 2004-24918.

As will be described later, even when measurements are to be taken a number of times separately by the MRI apparatus, it becomes possible to register the position and direction of slices, by the function as described above.

RF irradiating unit 16 irradiates a region of interest of subject 2 with RF (Radio Frequency) pulses based on a high-frequency signal transmitted from a signal transmitting unit 26 in accordance with a control sequence.

Though RF irradiating unit 16 is built in magnetic field applying mechanism 11 in FIG. 1, it may be mounted on bed 18 or integrated with receiving coil 20.

Receiving coil 20 detects a response wave (NMR signal) from subject 2, and in order to detect the NMR signal with high sensitivity, it is arranged close to subject 2.

Here, when an electromagnetic wave of NMR signal crosses a coil strand of receiving coil 20, a weak current is generated by electromagnetic induction. The weak current is amplified by signal receiving unit 28 and converted from an analog signal to a digital signal, and then transmitted to data processing unit 32.

The mechanism here is as follows. Specifically, to a subject 2 in a state of static magnetic field with Z-axis magnetic field gradient added, a high-frequency electromagnetic field of resonance frequency is applied through RF irradiating unit 16. Then, prescribed atomic nuclei at a portion where magnetic field intensity satisfies the condition of resonance, for example, hydrogen atomic nuclei, are selectively excited and start resonating. Prescribed atomic nuclei at a portion satisfying the condition of resonance (for example, a slice of prescribed thickness of subject 2) are excited, and spins concurrently start rotation. When the excitation pulse is stopped, electromagnetic waves radiated by the rotating spins induce a signal in receiving coil 20 and, for some time, this signal is continuously detected. By this signal, a tissue containing the prescribed atoms in the body of subject 2 is monitored. In order to know the position where the signal comes from, X- and Y-magnetic field gradients are added and the signal is detected.

Based on the data built in storage unit 36, image processing unit 48 measures detected signals while repeatedly applying excitation signals, reduces resonance frequency to X-coordinate by a first Fourier transform, restores Y-coordinate by a second Fourier transform, and thus, displays a corresponding image on display unit 38.

Figure 2:
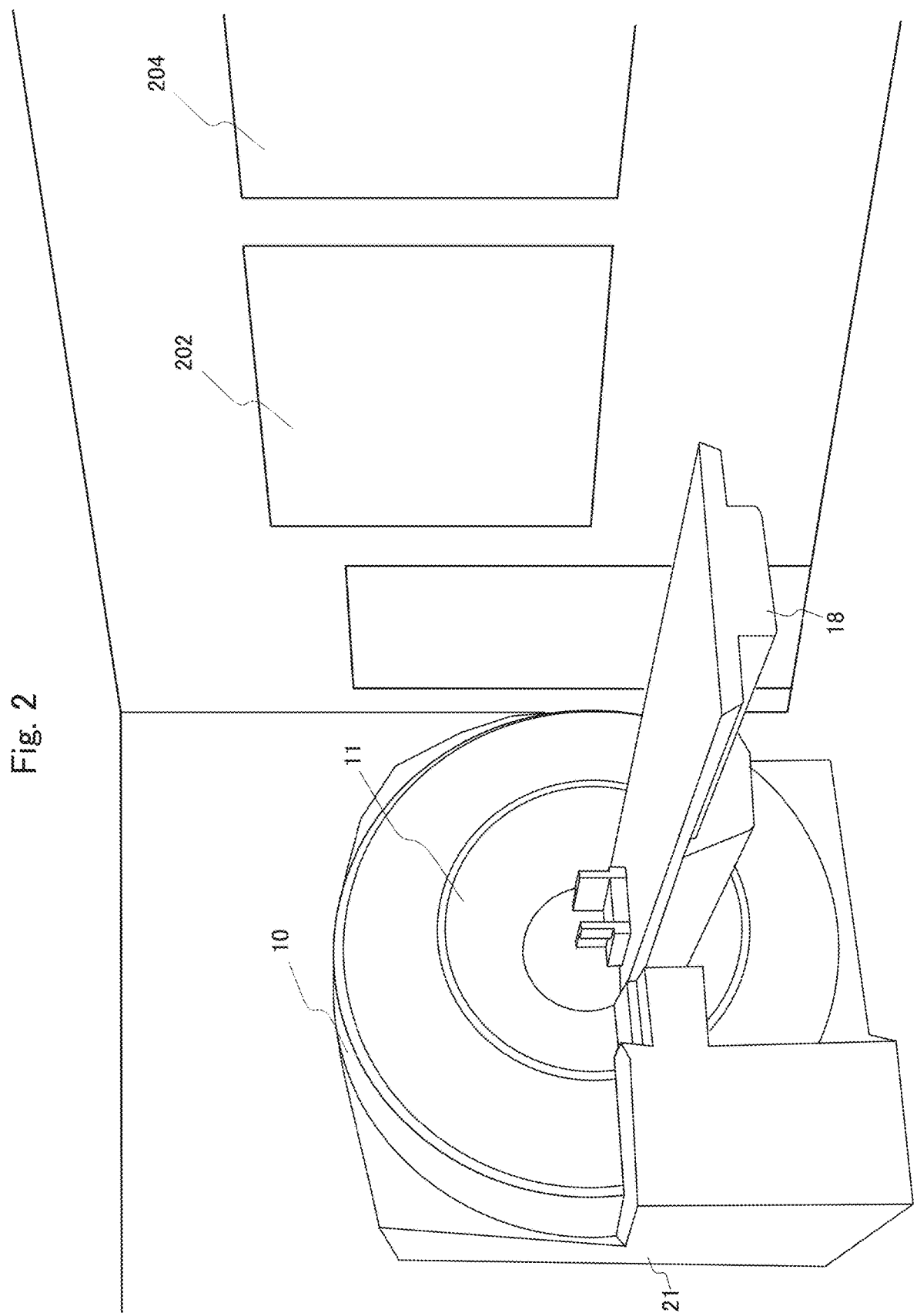
FIG. 2 is a perspective view showing an external configuration of MRI apparatus 10 and surrounding environment.

FIG. 2 is a perspective view showing an external configuration of MRI apparatus 10 and surrounding environment.

As shown in FIG. 2, in an environment where the MRI is installed, there is an operation room 202 in which a data processing unit 32 for operating MRI apparatus 10 is installed, and an anteroom 204 in which a terminal allowing monitoring of measurement results by an experimenter or the like of a different institution is installed.

Figure 3:
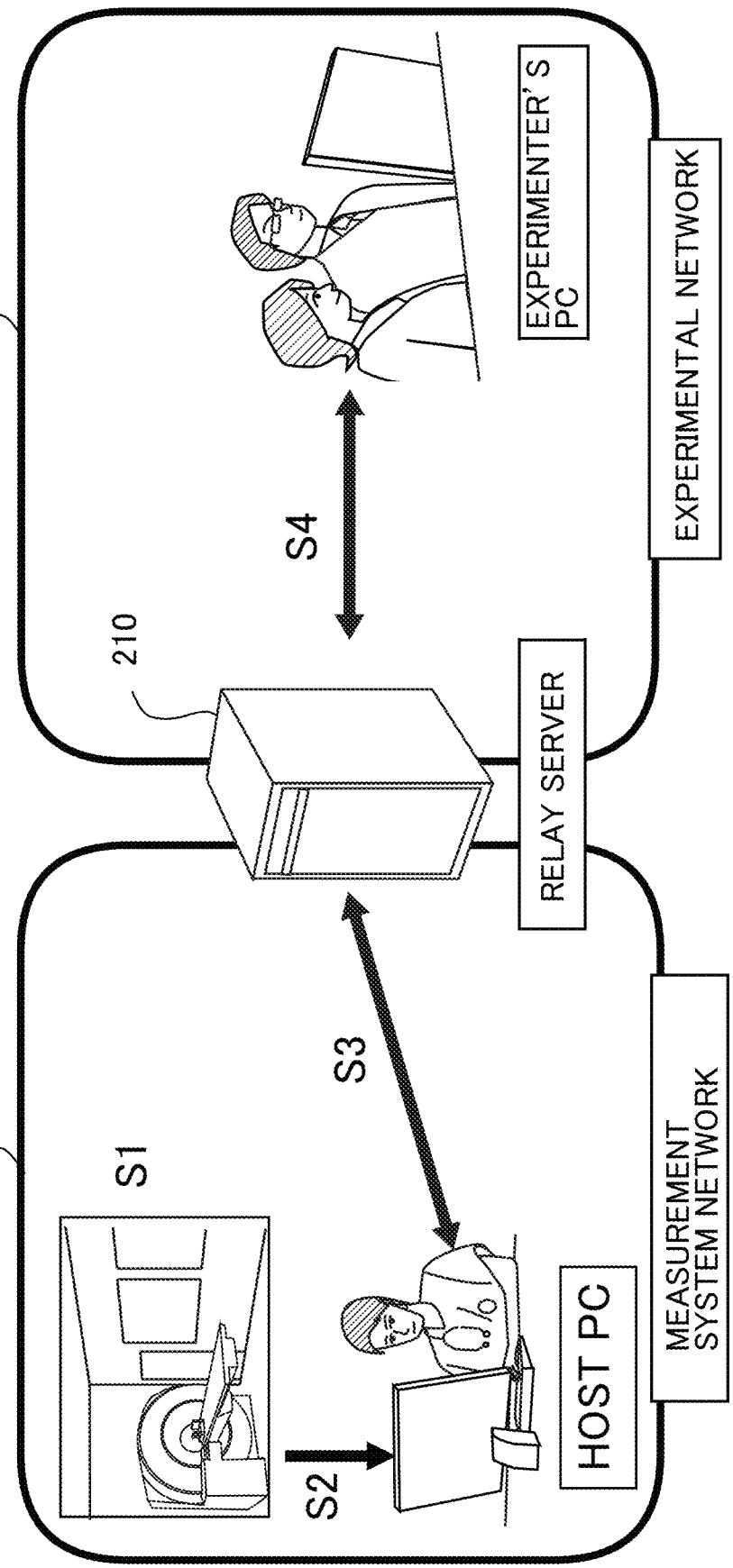
FIG. 3 is a conceptual illustration of a control system related to MRI apparatus 10.

FIG. 3 is a conceptual illustration of a control system related to MRI apparatus 10.

First, a measurement is taken by MRI apparatus 10 (S1), and the measured data is transferred to a host PC (data processing unit 32) (S2). An operator controls MRI apparatus 10 through the host PC. Further, the data that has been transferred to the host PC is transferred to a relay server 210 (S3).

In anteroom 204, an experimenter monitors on real-time basis the data that has been transferred through relay server 210 to a PC of the experimenter (S4).

The PC of the experimenter is configured to receive transfer of only the data related to his/her experiment through relay server 210, and the PC of the experimenter cannot access to any data other than those of the subject of the experiment.

Particularly, in an experiment in accordance with the DecNef method described above, the process is as follows.

(1) The position of imaging of the subject today is registered with past positions of imaging of the same subject (position registration of MRI imaging slice).

(2) MRI data is output on real-time basis to the host PC.

(3) The MRI data of host PC is copied to the relay server (file transfer of MRI imaging data).

(4) The experimenter accesses to the file in the relay server from the experimenter's PC.

Details of (1) position registration of MRI imaging slice and (3) file transfer of MRI imaging data will be described later.

Figure 4:
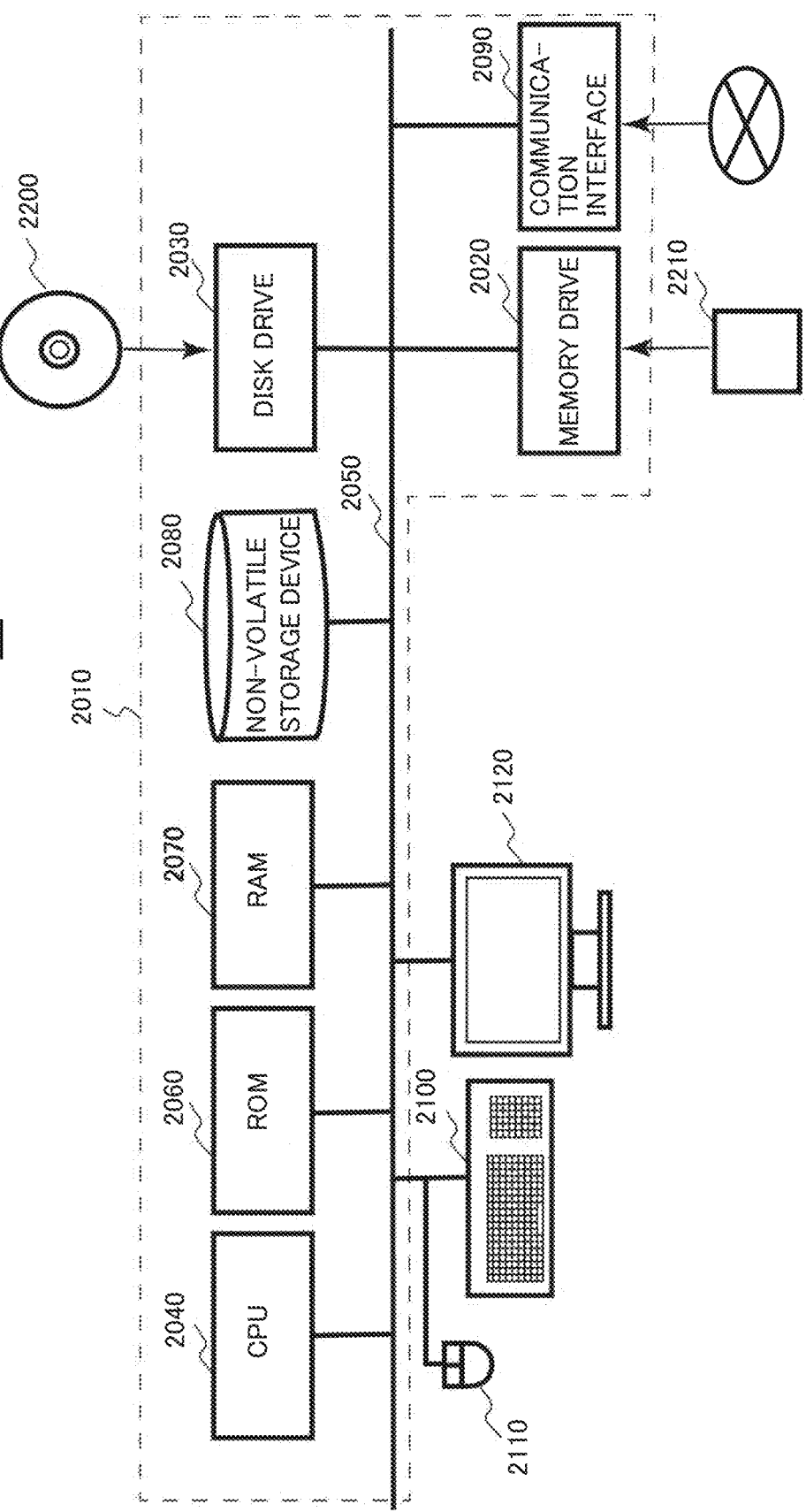
FIG. 4 is a hardware block diagram of a host PC (data processing unit 32).

FIG. 4 is a hardware block diagram of a host PC (data processing unit 32).

Though the hardware of data processing unit 32 is not specifically limited, a general-purpose computer may be used.

Referring to FIG. 4, a computer main body 2010 of data processing unit 32 includes, in addition to a memory drive 2020 and a disk drive 2030, a CPU 2040, a bus 2050 connected to disk drive 2030 and memory drive 2020, an ROM 2060 for storing programs such as a boot-up program, an RAM 2070 for temporarily storing instructions of an application program and providing a temporary memory space, a non-volatile storage device 2080 for storing an application program, a system program and data, and a communication interface 2090 for communication with MRI apparatus 10 and relay server 210. As non-volatile storage device 2080, a hard disk (HDD), a solid state drive (SSD) or the like may be used.

By operation processes executed by CPU 2040 in accordance with a program, various functions of data processing unit 32 are realized.

A program or programs causing data processing unit 32 to execute the function of the present embodiment as described above may be stored in a CD-ROM 2200 or a memory medium 2210 and inserted to disk drive 2030 or memory drive 2020 and may further be transferred to non-volatile storage device 2080. The program is loaded to RAM 2070 before execution.

Data processing unit 32 further includes a keyboard 2100 and a mouse 2110 as input devices, and a display 2120 as an output device.

The program realizing the function of data processing unit 32 as described above may not necessarily include an operating system (OS) for executing the function of information processing apparatus such as computer main body 2010. The program may only include those portions of instructions which can call appropriate functions (modules) in a controlled manner to attain a desired result. The manner how data processing unit 32 operates is well known and, therefore, detailed description will not be given here.

It is noted that one or a plurality of computers may be used to execute the program described above. In other words, either centralized or distributed processing may be possible.

Relay server 210 and the experimenter's PC also have hardware configurations similar to that of data processing unit 32 and, therefore, description thereof will not be repeated.

(Position Registration of MRI Imaging Slice)

In the process of position registration of MRI imaging slice, the position of slicing of MRI head imaging data to be newly taken at a certain measurement session (a certain day of measurement) is automatically registered with the position of slicing of past MRI head imaging data. This is to reduce error.

Neurofeedback such as the DecNef Method involves a process of measuring time-sequential effects of learning by a subject based on fMRI measurements, and a process of feeding back information calculated from the result of measurements to the subject. In order to realize measurements less prone to error, it is essential to register the position of slicing of past fMRI measurements with the present position.

Figure 5:
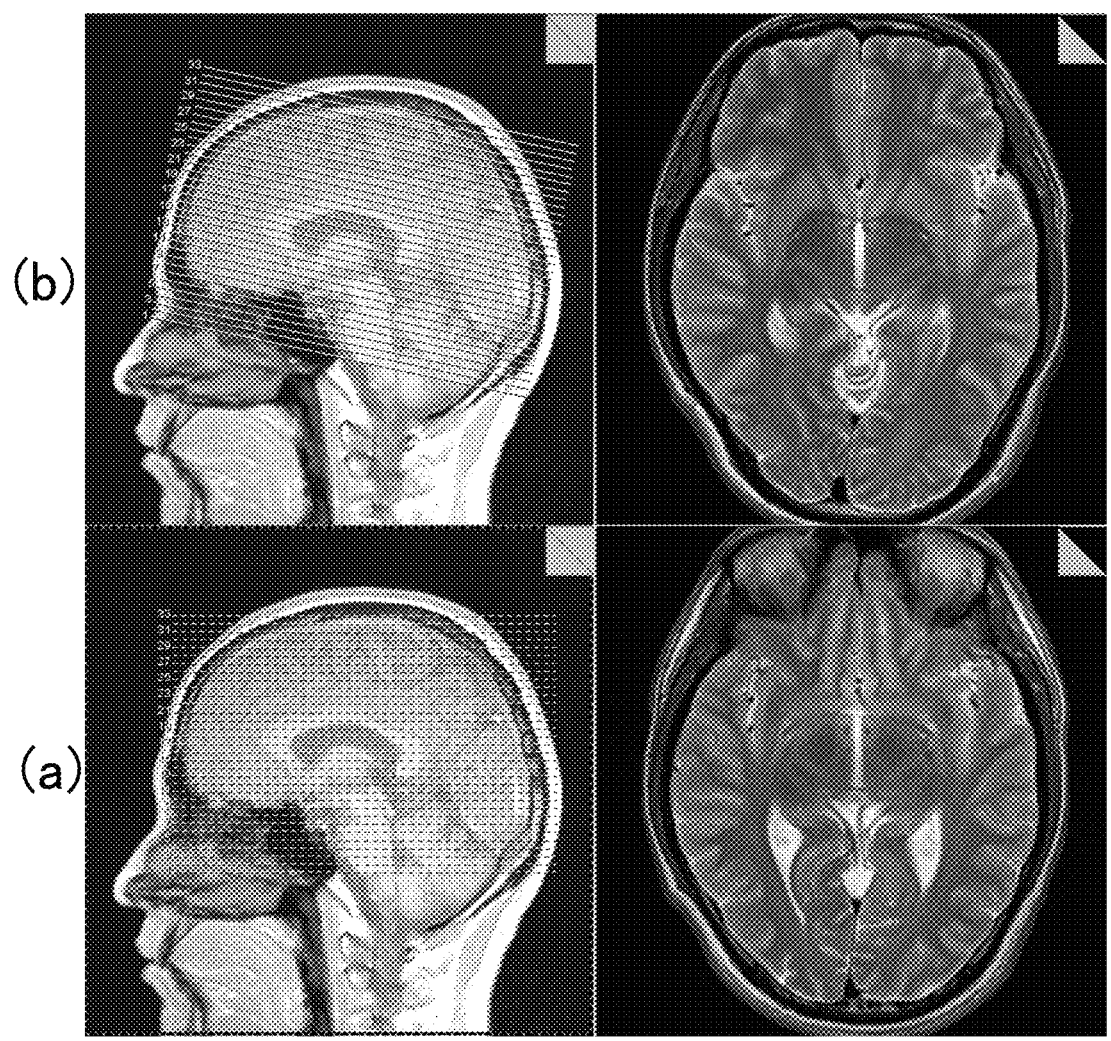
FIG. 5 shows, in comparison, positions of slices in the past and positions of slices in a process of new measurement.
Figure 6:
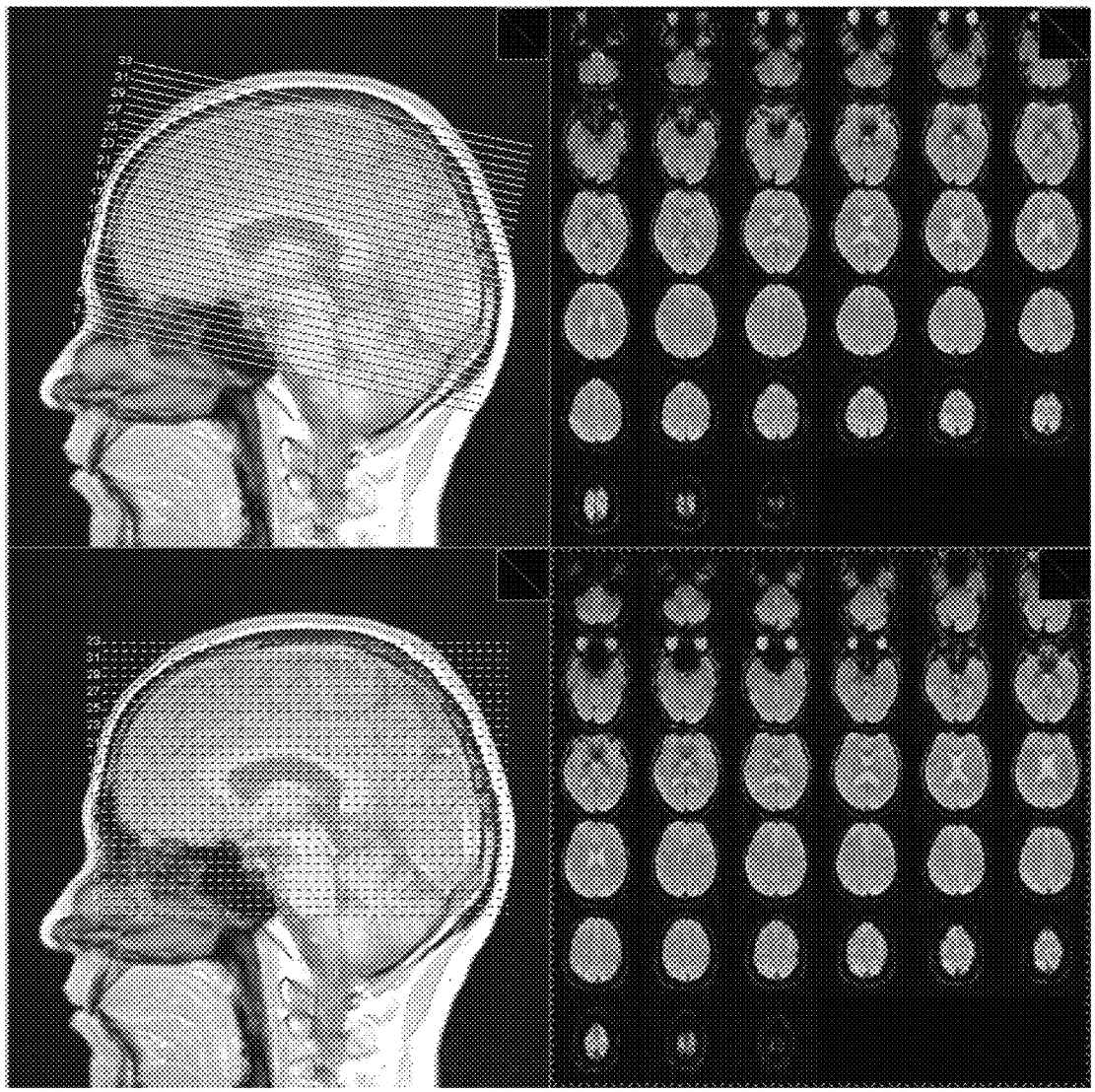
FIG. 6 shows, in comparison, positions of slices in the past and positions of slices in a process of new measurement.

FIGS. 5 and 6 show, in comparison, positions of a past slice and positions of a slice of which measurement is to be newly started.

FIG. 5(a) and FIG. 6(a) both show the slice position and cross-sectional image of past MRI head imaging data, and FIG. 5(b) and FIG. 6(b) show slice position of the imaging data when the head is to be newly imaged by MRI.

Though exaggerated to some extent in FIGS. 5 and 6, when imaging is reset and started anew, for example, on a different day, the position and direction (tilt) of slicing are not necessarily the same.

As a result, even when slice images are positioned with their centers placed substantially on the same position, these images are not registered in the entirety. When fMRI images are to be used for neurofeedback, it is necessary to feedback information based on the result of measurements to the subject based on the data measured on real-time basis from a specific brain region. Therefore, such difference in the position and direction (tilt) of slicing affects the precision of experiments.

Though the position of slice can be adjusted by image processing after the end of measurement, this approach has problems that the resolution becomes lower and it takes time to calculate.

It is also possible to adjust the position and tilt of slicing manually. This approach, however, has the following problems.

i) High skill and proficiency are required to enable registration with minimum error.

ii) Visual comparison with past fMRI images takes long time.

iii) Quality of registration varies even when handled by one operator.

In view of the foregoing, the present embodiment incorporates a process of registering positions and directions (tilt) of slices for two different measurements, using mutual information between two images, before starting the measurement.

In connection with position registration between images obtained by different methods of imaging such as MRI and PET (multimodal images), the following reference discloses mutual information between such images and position registration using the mutual information.

REFERENCE

Frederik Maes, Andre Collignon, Dirk Vandermeulen, Guy Marchal, and Paul Suetens, "Multimodality Image Registration by Maximization of Mutual Information", IEEE TRANZACTIONS ON MEDICAL IMAGING, VOL. 16, No. 2, April, 1997, pp. 187-198.

REFERENCE

Andre Collignon, Fredrik Maes, Deminique Dlaere, Dirk Vandermeulen, Paul Suetens, Guy Marchal, "Automated multimodality image registration based on information theory", Information processing in medical imaging (1995), Volume: 3, Issue: 6, Pages: 263-274.

REFERENCE

SHINOHARA Hiroyuki, ITO Takeshi, IMAI Takahiro, ITO Kenji, HASHIMOTO Takeyuki, "Dansou Eizou hou no kiso dai 20 kai, gazou no sougo jyouhou ryo" (Basics of Tomographic Imaging, 20th Lecture, Mutual Information of Images), Journal of Japanese Association of Tomography, Vol. 33, No. 3, pp. 154-160.

Figure 7:
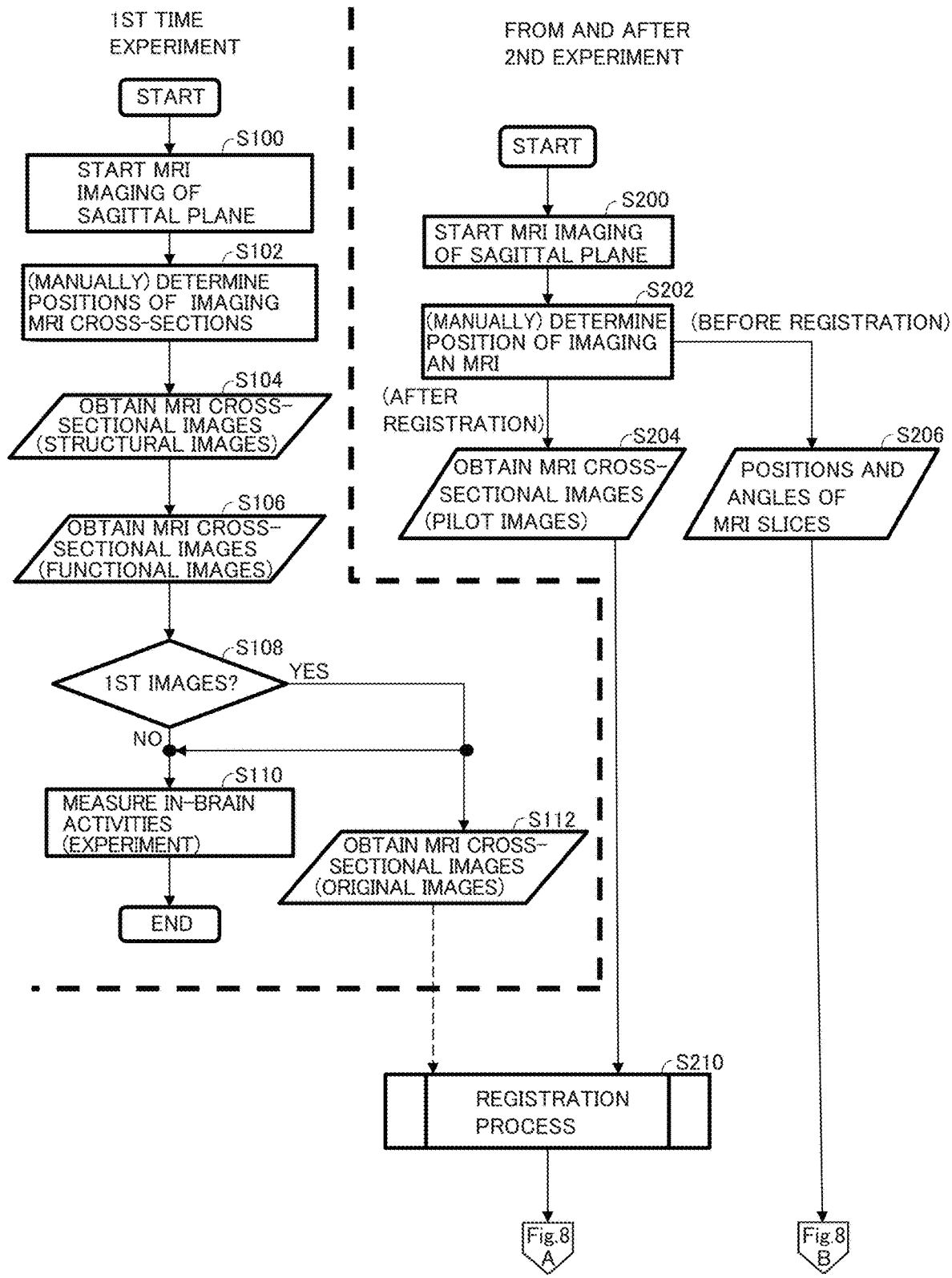
FIG. 7 is a flowchart representing a process of registering MRI imaging slices.
Figure 8:
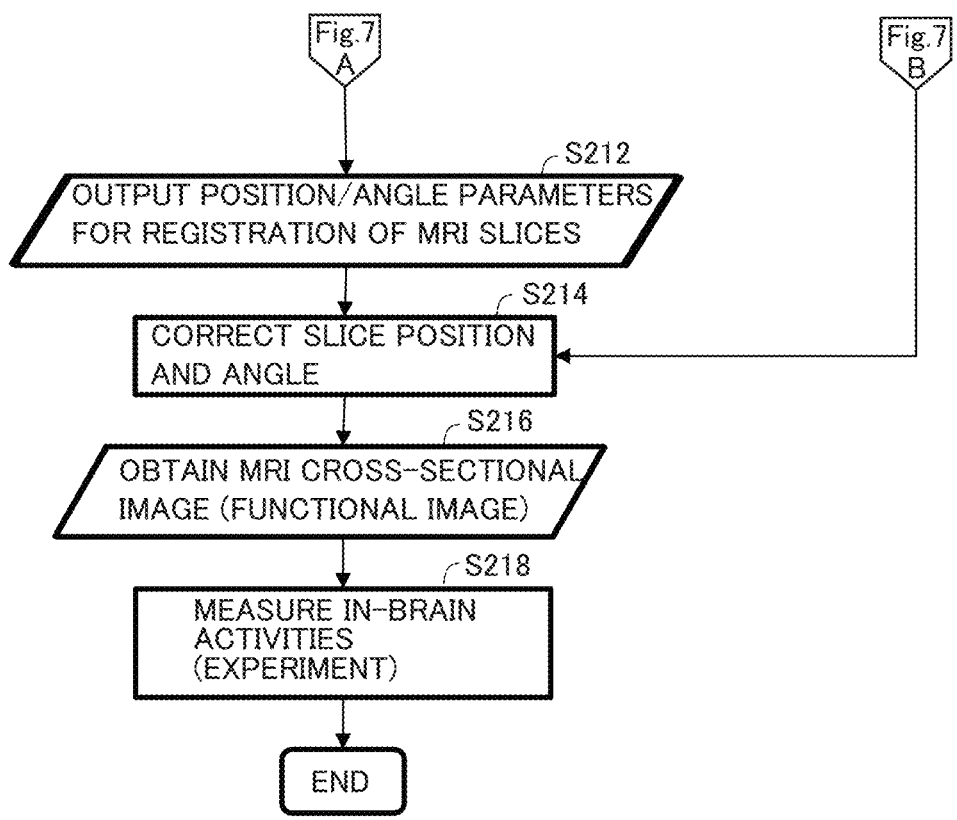
FIG. 8 is a flowchart representing a process of registering MRI imaging slices.

FIGS. 7 and 8 are flowcharts representing a process of registering MRI imaging slices.

When the first measurement starts, MRI sagittal plane image is obtained (S100). Thereafter, based on this sagittal plane image, an operator manually determines a position for MRI cross section imaging, and inputs an imaging position (S102).

Thereafter, MRI cross section imaging takes place, and a structural image is obtained (S104). An MRI cross section imaging takes place for a functional image (S106) and, if it is the first image, it is registered with storage unit 36 as an original image of MRI cross section (S112).

For the second and the following images, measurements of brain activities are executed utilizing the functional imaging of fMRI (S110).

For the second and the following experiments, when the experiment starts, the MRI sagittal plane image is obtained (S200). Thereafter, if it is before the registration process, based on the sagittal plane image, the operator manually determines the position and angle of slicing the present MRI image for the functional imaging (S202), and takes an image (pilot image) (S204).

The conditions (slice thickness, number of slices, view angle, resolution and the like) for taking the pilot image are the same as those for the original image except for the position and angle of slicing. The position and angle of slicing are determined by horizontal movement of three axes as well as by the angle of rotation of the three axes with respect to the origin of MRI coordinate system.

Thereafter, data processing unit 32 registers the original image and the pilot image (S210).

In the registration process, deviation between the two images is modeled by rigid transformation having the horizontal movement of three axes and the angle of rotation of three axes as transformation parameters. Using mutual information as a degree of image similarity, a transformation parameter that locally maximizes the mutual information is calculated by an optimization algorithm such as Powell conjugate direction method.

By the registration process, the parameters for the position and angle of slicing are calculated to minimize any error of the position and angle of pilot image with respect to the original image, and stored in storage unit 36 (S212). The position and angle of slicing are corrected (S214), an MRI cross section image (functional image) is taken (S216), and the measurements of brain activities are executed (S218).

In a process in which a measurement is executed after the registration, the position and angle of MRI slicing stored in storage unit 36 are read (S206), and the process steps from S214 are executed.

Figure 9:
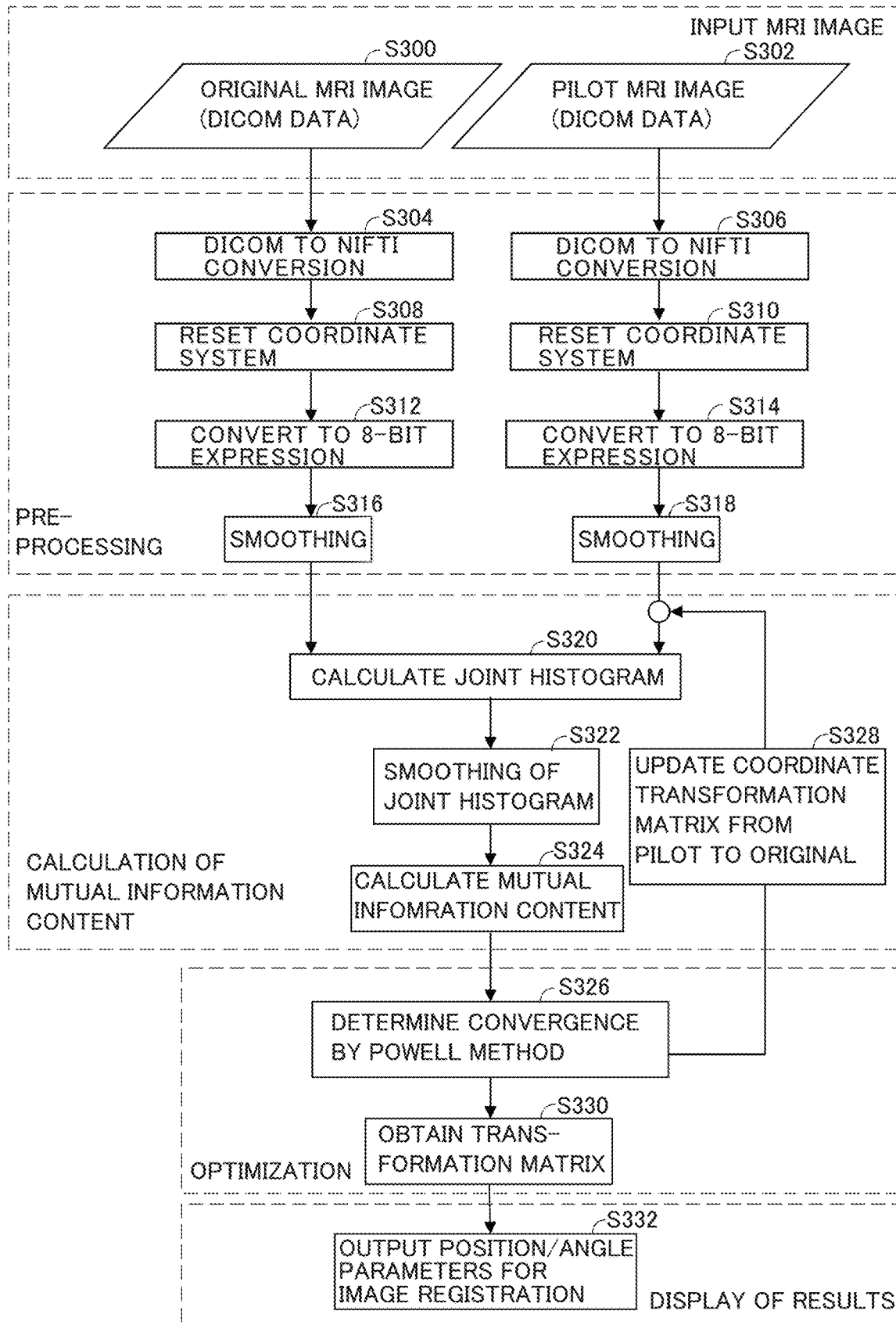
FIG. 9 is a flowchart representing a process of registering MRI imaging slices.

FIG. 9 is a flowchart representing the process of registering shown in FIG. 7.

In data processing unit 32, the original MRI image (DICOM (Digital Imaging and Communications in Medicine) data) and the pilot MRI image (DICOM data) are read from storage unit 36 (S300, S302).

Each of the original image and the pilot image is converted from the DICOM data to Nifti format (S304, S306).

Thereafter, both images have their coordinate systems reset (S308, S310), each image is converted, for example, to 8-bit tone-image and subjected to smoothing process (S312, S314, S316, S318).

Data processing unit 32 calculates a joint histogram from the two images (S320), and smoothes the joint histogram (S322).

Data processing unit 32 calculates the mutual information from the smoothed joint histogram. (S324).

Here, we represent the original MRI image as f, pilot MRI image as g, and a transformation matrix of rigid transformation having the horizontal movement of three axes and the rotation angle of three axes as transformation parameters as M.

The mutual information is given by the following equation, where H( . . . ) represents mean information content (entropy).

$$NMI(g, f) = \frac{H(g) + H(f)}{H(g, f)},$$

Image entropy: $H(x) = \int_{-\infty}^{+\infty} P(x) \log P(x) dx$.

The transformation matrix M is calculated as follows.

$\hat{M} = {}_M \text{argmax } NMI(g(x), f(Mx))$.

Actually, until the transformation matrix is obtained, the process is repeated until the mutual information is locally maximized (or maximized) and converged while successively updating the transformation matrix using the conjugate direction method (Powell method) or the like (S326, S328).

When the transformation matrix M is obtained in this manner (S330), it is output as the position/angle parameter for image registration and stored in storage unit 36 (S332).

The head position of a subject in the MRI apparatus differs on the first day and on the second and following days. Therefore, strictly speaking, even when the position of slicing defined in the coordinate system of the MRI apparatus set at the time of MRI imaging on the first day is applied directly on the second and later days, the resulting cross sections of the head of MRI images are not the same. Therefore, more specifically, calculation is done to obtain the images of the same cross section on the coordinate system of MRI image (tomographic image), and the result of calculation is converted to a position in the coordinate system of the MRI apparatus for the second and following days to be used for correcting the position of slicing on the second day and thereafter.

By the process as described above, it becomes possible to precisely ensure the reproducibility of measurements in functional magnetic resonance imaging performed a number of times separately.

(File Transfer of MRI Image Data)

In the file transfer process of MRI image data, the picked-up MRI image data for measuring brain activities is transferred to a relay server 210 simultaneously with the image pick-up.

When taking of MRI images for measuring brain activities ends, the images are output immediately thereafter as an image data file. It is desired to analyze the image data file by an analyzing PC and to provide feedback to the subject as numerical values or in the form of images. Considering the protection of patient's privacy, however, it is undesirable to directly connect the experimenter's PC to a host PC. Further, if an experimenter's PC, which is not originally configured as a system for controlling the MRI apparatus, is directly connected to the MRI apparatus, the experimental system may become unstable, as described above.

Figure 10:
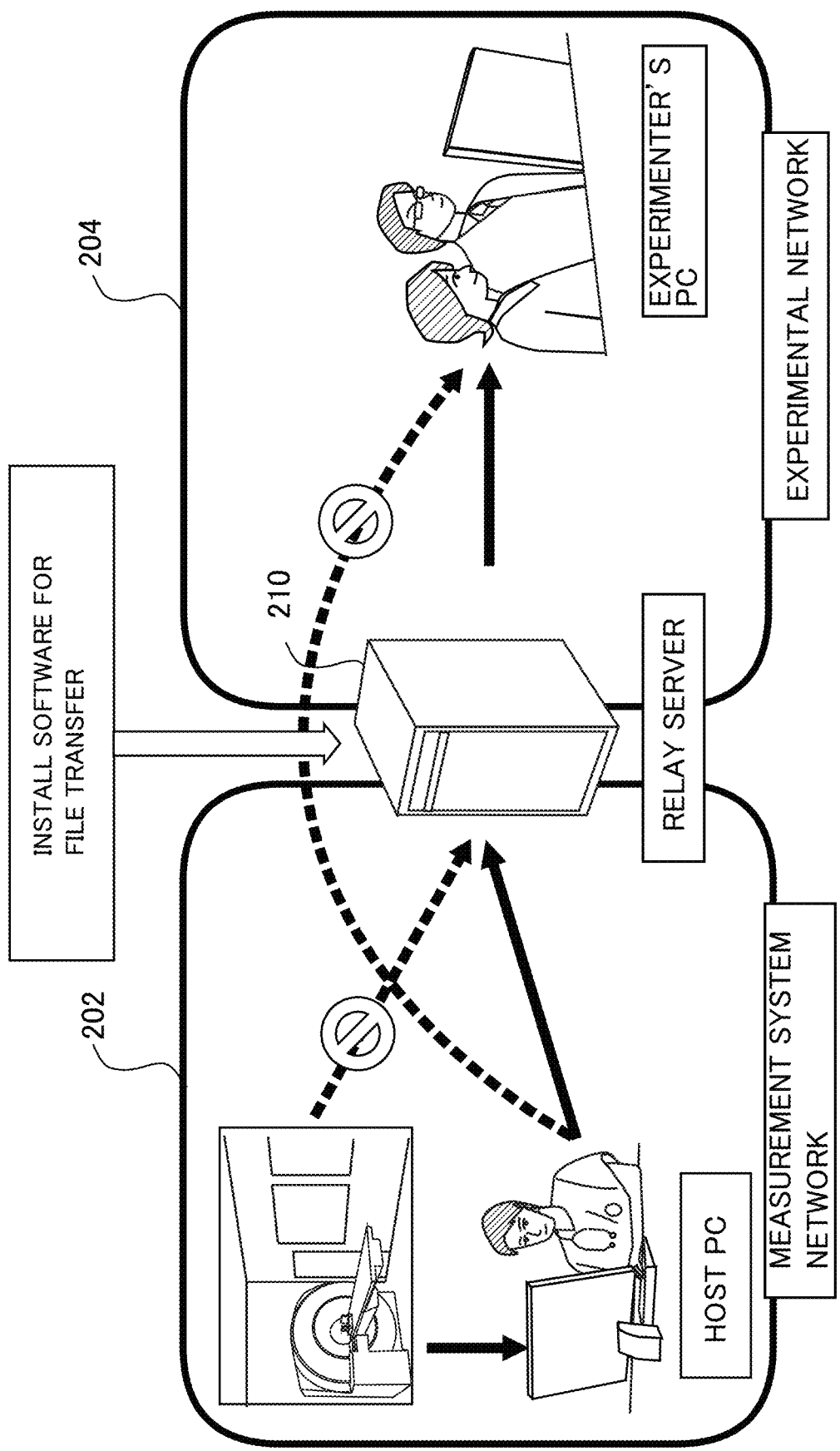
FIG. 10 illustrates connection relations between a host PC and a PC of an experimenter.
Figure 11:
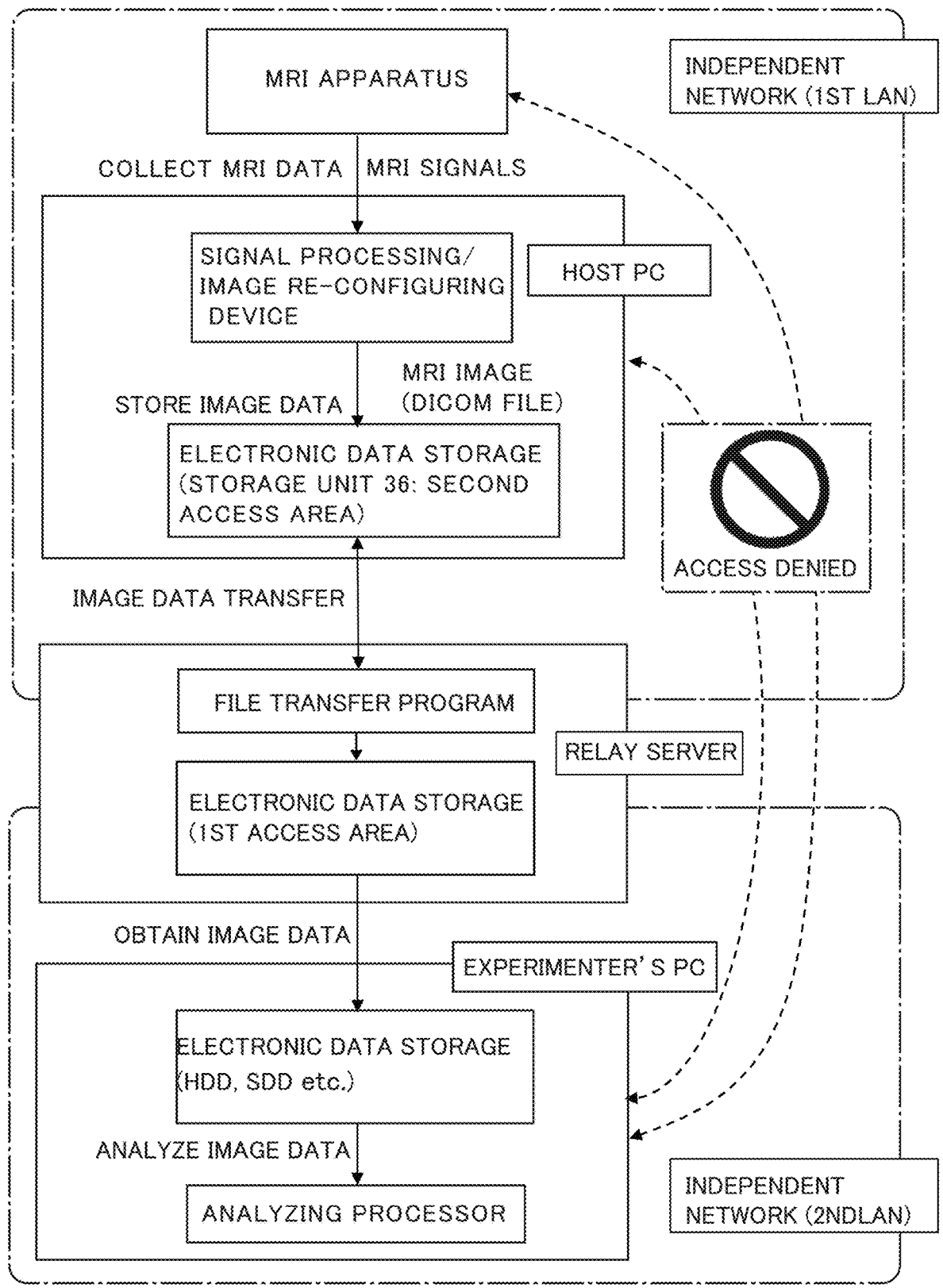
FIG. 11 illustrates connection relations between a host PC and a PC of an experimenter.

FIGS. 10 and 11 illustrate connection relations between a host PC and a PC of an experimenter.

As shown in FIG. 10, by providing a relay server 210, the network for the part related to MRI control (measurement system network) and the network for the part related to analysis (experimental system network) are made independent.

As shown in FIG. 11, in relay server 210, a first access area that can be accessed from the experimenter's PC through a file-sharing protocol such as SMB (Server Message Block) and CIFS (Common Internet File System) is prepared.

In the host PC also, a second access area that can be accessed from relay server 210 through a file-sharing protocol such as SMB and CIFS is prepared.

The MRI data output as a result of MRI imaging is output as an electronic file to the second access area of the host PC. A file transfer program that constantly monitors the second access area of the host PC and synchronized with the first access area is installed in relay server 210.

The experimenter's PC accesses to the first access area of relay server 210 and obtains the MRI data. Access from the experimenter's PC to the host PC or to the MRI apparatus is inhibited.

By the configuration as described above, stable operation becomes possible even when the operation is done by a plurality of operators, and the patient's privacy can be protected.

The embodiments as have been described here are mere examples and should not be interpreted as restrictive. The scope of the present invention is determined by each of the claims with appropriate consideration of the written description of the embodiments and embraces modifications within the meaning of, and equivalent to, the languages in the claims.

INDUSTRIAL APPLICABILITY

The brain activity measuring apparatus and the brain activity measuring method of the present invention can be applied to perceptual learning, rehabilitation for persons having disabilities, sports relaxation and the like.

REFERENCE SIGNS LIST

2 subject, 6 display, 10 MRI apparatus, 11 magnetic field applying mechanism, 12 static magnetic field generating coil, 14 magnetic field gradient generating coil, 16 RF irradiating unit, 18 bed, 20 receiving coil, 21 driving unit, 22 static magnetic field power source, 24 magnetic field gradient power source, 26 signal transmitting unit, 28 signal receiving unit, 30 bed driving unit, 32 data processing unit, 36 storage unit, 38 display unit, 40 input unit, 42 control unit, 44 interface unit, 46 data collecting unit, 48 image processing unit, 50 network interface.

The invention claimed is:

1. A brain activity measuring apparatus for detecting a detection signal caused by nuclear magnetic resonance from a subject to generate a tomographic image of a region to be measured, comprising:
   a static magnetic field applying device for applying a static magnetic field to said region to be measured;
   a magnetic field gradient applying device for applying to said region to be measured a magnetic field modulated such that said detection signal has positional information of an atomic nucleus emitting said detection signal in a selected cross-section of said region to be measured;
   an electro-magnetic wave transmitting/receiving device for applying an electro-magnetic wave to said region to be measured and detecting said detection signal from said region to be measured;
   a tomography control device for applying said electro-magnetic wave to said electro-magnetic wave transmitting/receiving device and receiving said detection signal to generate said tomographic image of a slice;
   a storage device for storing said generated tomographic image; and
   a network interface for communicating with a relay server through a measurement network, wherein
   said tomography control device
     i) determines three-dimensional rigid transformation between a reference tomographic image of said subject obtained in a past measurement and stored in said storage device and a preliminary tomographic image of said subject obtained in a present imaging session such that mutual information between said reference tomographic image and said preliminary tomographic image is locally maximized, and
     ii) based on a parameter of said determined rigid transformation, controls said magnetic field gradient applying device in the present imaging session and thereby corrects position and direction of the slice of tomographic imaging,
   said relay server transfers tomographic image data received via the network interface on the measurement network to a terminal device on an experimental network independent from said measurement network by synchronizing data stored in a first access area on the relay server with data from the measurement network by running a file transfer program that constantly monitors data stored in a second access area of the measurement network and syncs the data stored in the second access area with the data stored in the first access area and transferring the data stored in the first access area to the terminal device on the experimental network, the terminal device on the experimental network is prevented from directly accessing data on the measurement network.

2. The brain activity measuring apparatus according to claim 1, wherein said tomography control device corrects the position of the slice in a coordinate system of said brain activity measuring apparatus, based on the parameter of said rigid transformation determined in a coordinate system of the tomographic image by said reference tomographic image and said preliminary tomographic image.

3. The brain activity measuring apparatus according to claim 2, further comprising a presenting device for providing bio-feedback to said subject based on said generated tomographic image.

4. The brain activity measuring apparatus according to claim 3, wherein said bio-feedback is bio-feedback based on a decoded neuro-feedback method.

5. A brain activity measuring method for generating a tomographic image of a region of a subject to be measured by detecting a detection signal caused by nuclear magnetic resonance from the subject, the method comprising the steps of:

applying a static magnetic field to said region to be measured;

applying to said region to be measured a magnetic field modulated such that said detection signal has positional information of an atomic nucleus emitting said detection signal in a selected cross-section of said region to be measured;

applying an electro-magnetic wave to said region to be measured and detecting said detection signal from said region to be measured;

receiving said detection signal and generating said tomographic image of a slice;

storing said generated tomographic image in a storage device; and communicating via a network interface with a relay server through a measurement network to transfer the generated tomographic image stored in the storage device to the relay server, wherein said step of generating said tomographic image includes the steps of determining three-dimensional rigid transformation between a reference tomographic image of said subject obtained in a past measurement and stored in said storage device and a preliminary tomographic image of said subject obtained in a present imaging session such that mutual information between said reference tomographic image and said preliminary tomographic image is locally maximized, and based on a parameter of said determined rigid transformation, controlling a magnetic field gradient applying device during the present imaging session thereby correcting a position and direction of the slice of tomographic imaging, said relay server transfers tomographic image data received via the network interface on the measurement network to a terminal device on an experimental network independent from said measurement network by synchronizing data stored in a first access area on the relay server with data from the measurement network by running a file transfer program that constantly monitors data stored in a second access area of the measurement network and syncs the data stored in the second access area with the data stored in the first access area and transferring the data stored in the first access area to the terminal device on the experimental network, the terminal device on the experimental network is prevented from directly accessing the data on the measurement network.

6. The brain activity measuring method according to claim 5, wherein controlling the magnetic field gradient applying device, includes correcting the position of the slice in a coordinate system of a brain activity measuring apparatus, based on the parameter of said rigid transformation determined in a coordinate system of the tomographic image by said reference tomographic image and said preliminary tomographic image.

* * * * *